United States Patent [19]

Jacquet et al.

[11] Patent Number: 4,826,681

[45] Date of Patent: May 2, 1989

[54] ANHYDROUS SOLUTION OF HYDROGEN PEROXIDE IN AN ORGANIC SOLVENT AND THE USE OF THE SAME IN THERAPEUTIC AND COSMETIC FORMULATIONS

[75] Inventors: Bernard Jacquet, Antony; Quintino Gaetani, Bondy; Michel Hocquaux, Paris, all of France

[73] Assignee: L'Oreal, Paris, France

[21] Appl. No.: 833,005

[22] Filed: Feb. 26, 1986

[30] Foreign Application Priority Data

Feb. 26, 1985 [LU] Luxembourg .......................... 85789

[51] Int. Cl.⁴ ..................... A61K 9/00; A61K 47/00; C01B 15/02
[52] U.S. Cl. .................................... 424/613; 424/62; 514/714; 514/844; 514/859
[58] Field of Search ................ 424/62, 130; 514/714, 514/827, 828, 859, 844

[56] References Cited

U.S. PATENT DOCUMENTS

| | | | |
|---|---|---|---|
| 1,154,021 | 6/1969 | D'Aveze | 424/62 |
| 2,015,179 | 9/1935 | McGraw | 424/62 |
| 3,480,557 | 11/1969 | Shiraeff | 424/62 |
| 3,969,516 | 7/1976 | Stoughton | 514/859 |
| 4,170,637 | 10/1979 | Pum | 424/62 |
| 4,466,955 | 8/1984 | Calvo et al. | 424/62 |
| 4,532,125 | 7/1985 | Vanlerberghe et al. | 424/62 |
| 4,608,392 | 8/1986 | Jacquet et al. | 514/859 |
| 4,609,674 | 9/1986 | Gupte | 514/714 |
| 4,656,030 | 4/1987 | Sebag et al. | 424/62 |

FOREIGN PATENT DOCUMENTS

| | | | |
|---|---|---|---|
| 1347285 | 12/1962 | France | 424/62 |
| 0465188 | 6/1937 | United Kingdom | 424/62 |
| 0821726 | 10/1959 | United Kingdom | 424/62 |
| 2076285 | 12/1981 | United Kingdom | 514/714 |

*Primary Examiner*—Ronald W. Griffin
*Assistant Examiner*—Nancy S. Carson
*Attorney, Agent, or Firm*—Cushman, Darby & Cushman

[57] ABSTRACT

A liquid, essentially anhydrous solution of hydrogen peroxide in at least one organic solvent is employed in therapeutic and cosmetic formulations. The solution contains from 1 to 20 weight percent hydrogen peroxide and less than 1 weight percent water. The therapeutic formulation can be used in the treatment of acne, dermatoses, ulcers and in the lightening and disinfection of the skin. The cosmetic formulations can be used in the bleaching or oxidation dyeing of hair or in the neutralization stage of a permanent wave operation or in the straightening of hair.

11 Claims, No Drawings

ANHYDROUS SOLUTION OF HYDROGEN PEROXIDE IN AN ORGANIC SOLVENT AND THE USE OF THE SAME IN THERAPEUTIC AND COSMETIC FORMULATIONS

The present invention relates to an anhydrous solution of hydrogen peroxide in an organic solvent and to the use of said solution in therapeutic and cosmetic formulations.

Hydrogen peroxide in an aqueous solution, or oxygenated water, is well known for its oxidizing and bactericidal properties. Oxygenated water is particularly recommended for cutaneous or buccal disinfection, for the disinfection of wounds and hands, and in the treatment of mycoses, inflammations and ulcers. Oxygenated water is quite particularly useful in the treatment of acne and other skin diseases by inhibiting the growth of the principal strains of bacteria responsible for acne manifestations.

The oxidizing properties of oxygenated water are desirable in cosmetic formulations not only for bleaching or oxidation dyeing of the harir, but also in permanent wave operations as neutralization or fixation agents.

Solutions of oxygenated water generally employed contain 6 or 9% (20 or 30 volumes) of hydrogen peroxide. However, under certain conditions, solutions containing hydrogen peroxide in higher concentrations, such as for example, 30% (100 volumes) can also be employed.

It has been observed that dilute solutions of hydrogen peroxide exhibit the disadvantage of lacking stability over time, although this stability can be improved by the addition of a stabilizing agent. In the topical treatments mentioned above, and particularly in the treatment of acne, poor penetration of hydrogen peroxide into the skin and the appearance of a pronounced drying of the skin have been observed. Further, if the skin is exposed to an excessive amount of hydrogen peroxide, certain tissular lesions have been noted.

To remedy these various disadvantages, and principally that of the lack of stability of oxygenated water, and to assure better availability of the hydrogen peroxide, the present invention proposes the use of an essentially anhydrous solution of hydrogen peroxide in therapeutic and cosmetic formulations.

The anhydrous solutions of hydrogen peroxide, according to the present invention, can be used either in the therapeutic field, principally in the treatment of acne, or in the cosmetic field, more particularly in the capillary field, in hair bleaching operations, oxidation dyeings and in the neutralization stage of a permanent wave, or in uncurling or straightening the hair.

The present invention thus relates to the use of a liquid, essentially anhydrous solution of hydrogen peroxide, in at least one organic solvent, in therapeutic and cosmetic formulations, the said solution containing from 0.1 to 20 percent by weight of hydrogen peroxide and less than 1 percent by weight of water.

According to a preferred embodiment, the solution contains hydrogen peroxide in an amount ranging from 1 to 10 percent by weight and water in an amount lower than 0.5 weight percent, based on the total weight of said solution.

The nature of the organic solvent in which the hydrogen peroxide is dissolved can be quite varied. It is preferred however, in the practice of the present invention to use the following organic solvents which are therapeutically and cosmetically acceptable:

(1) alcohols having from 2 to 20 carbon atoms, such as ethanol, n-propanol, isopropanol, cyclohexanol, amyl alcohol, oleyl alcohol and benzyl alcohol;

(2) polyols such as glycols and, more particularly, ethylene glycol, propylene glycol, diethylene glycol, glycerol, and their ethers;

(3) ether oxides such as ethyl ether, isopropyl ether and dioxane;

(4) esters having the formula R'COOR" wherein R' has 1-21 carbon atoms and R" has 1-22 carbon atoms, such as ethyl acetate, butyl acetate, isopropyl myristate, isopropyl palmitate, isopropyl linoleate, arachidonyl propionate or a mixture of esters such as jojoba oil;

(5) triglycerides of fatty acids having from 6 to 22 carbon atoms, such as vegetable oils or those sold by Dynamit Nobel under the trade designations, "Miglyol 810" and "Miglyol 812";

(6) hydrocarbons such as petrolatum oil, perhydrosqualene, hydrogenated polyisobutene and the like;

(7) N-alkyl lactams having the formula

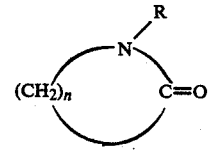

wherein
R is lower alkyl having 1–4 carbon atoms, and
n is a whole number ranging from 2 to 5, and particularly, N-methyl pyrrolidone;

(8) silicone oils; and (9) polyether oligomers, such as those of ethylene oxide, propylene oxide and their ethers, as well as polyether oligomers having the formula:

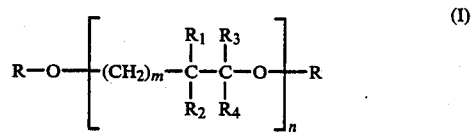

wherein
R represents linear or branched alkyl having 1–12 carbon atoms;
$R_1$, $R_2$, $R_3$ and $R_4$ each independently represent hydrogen or alkyl having 1–6 carbon atoms, with at least two of $R_1$, $R_2$, $R_3$ and $R_4$ representing hydrogen,
m is 1–4, and
n has a mean value greater than or equal to 2, and preferably between 4 and 50,
the number of carbon atoms in each repeating unit, identical or different, being at least equal to 4.

The average molecular mass of these polyether oligomers is generally between 200 and 5,000 and their viscosity ranges between 2 and 1,000 centipoises, preferably between 10 and 100 centipoises, measured at 25° C.

Among the polyether oligomers represented by the above formula, those providing excellent results in the therapeutic field, as well as in the cosmetic field, include the dimethyl ether of polytetrahydrofuran having the formula

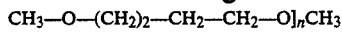
$CH_3-O-[(CH_2)_2-CH_2-CH_2-O]_nCH_3$ wherein n has a mean value between 4 and 10.

The organic solvent employed must, of course, be stable in the presence of hydrogen peroxide, this solvent being selected as a function of the use to which the anhydrous solution is employed.

The processes for the preparation of the anhydrous solutions of hydrogen peroxide are known and have been extensively described in the literature.

To prepare solution for use according to the present invention, two different procedures are envisaged according to the nature of the organic solvent.

When the organic solvent is not miscible with water, the hydrogen peroxide is extracted, with vigorous stirring, starting with a 60% aqueous solution of oxygenated water (200 volumes).

After stirring between 3 to 8 hours, the aqueous phase is saturated with sodium chloride and the organic phase is decanted and then dried on sodium sulfate.

When the organic solvent is miscible with water, the water is removed by azeotropic distillation. In this case, there is used, in admixture with the organic solvent, a co-solvent exhibiting the capability of forming an azeotropic mixture with water.

Representative solvents which are miscible with water and which can be used for the preparation of anhydrous solutions of hydrogen peroxide include, principally, such alcohols as ethanol, n-propanol, isopropanol and cyclohexanol; polyols such as ethylene glycol, propylene glycol and glycerol; ethers such as dioxane and tetrahydrofuran and polyether oligomers such as those of ethylene oxide, propylene oxide and their ethers.

In the situation where a co-solvent, capable of forming an azeotropic mixture with water is employed, the co-solvent can be, for instance, acetonitrile, tert. butanol, cyclohexane, heptane, pentane, 1,2-dichloroethane or ethyl acetate.

The azeotropic entrainment of water is made at the boiling temperature of the mixture. Thereafter, the hydrogen peroxide solution is cooled and dried on anhydrous sodium sulfate.

The amount of the hydrogen peroxide in the organic solvent is then determined by polarography.

As a function of the nature of the solvent, the amount of hydrogen peroxide in the solutions can vary widely.

Thus, when using the dimethyl ether of polytetrahydrofuran, having a viscosity of 22 centipoises at 25° C., it is possible to extract up to 15 percent of hydrogen peroxide, whereas when using amyl alcohol, the amount of hydrogen peroxide extracted is in the order of 7.6 percent.

Theoretically, anhydrous solutions of hydrogen peroxide can be obtained starting with a more concentrated oxygenated water, although their use is generally governed by convenience and, especially, safety reasons. Preferably, a 60% solution of hydrogen peroxide is employed initially.

An azeotropic distillation process is disclosed, for instance, in European patent application No. 0121660 published Oct. 17, 1984.

The anhydrous solutions of hydrogen peroxide are particularly useful in the treatment of acne and other skin disorders, in the treatment of ulcers and in the lightening of the color of the skin and in disinfecting the skin.

In this type of use, the organic solvent must be selected from those exhibiting good skin penetration and which do not cause any skin irritation.

Representative organic solvents which are appropriate for this use include n-propanol, isopropanol, benzyl alcohol, polyethylene glycols, polyethers of tetrahydrofuran, the monoethyl ether of diethylene glycol, the monoethyl ether of propylene glycol, triglycerides of saturated fatty acids having 8–12 carbon atoms, propylene glycol, silicone oils and N-alkyl lactams.

A particularly preferred solvent is the dimethyl ether of polytetrahydrofuran of which a 3% solution of hydrogen peroxide leads to comedolytic properties equal to those of a 6% solution of benzoyl peroxide in the rhino mouse test. It has been observed, in contrast, that an equivalent amount of hydrogen peroxide in an aqueous medium does not lead to any activity.

If the amount of hydrogen peroxide in the anhydrous solution is too high for the type of treatment contemplated, it is possible to dilute it with a desired amount of an extraction solvent or any other miscible solvent so as to provide an acceptable homogeneous solution.

The anhydrous solutions of hydrogen peroxide of the present invention can also contain other components, principally products which increase the viscosity thereof, so as to avoid undesirable solution run-off or flow during application.

In the capillary field, the anhyrous solutions of hydrogen peroxide, according to the invention, can be employed to bleach the hair so as to impart thereto a lighter appearance. These solutions can also be employed as an oxidizing agent in oxidation dyeing or in the second phase of a permanent waving operation to reform the S—S bonds or bridges of the keratin of the hair.

In this type of use, the compositions are provided, preferably, in the form of more or less thick solutions. These compositions can also contain various adjuvants conventionally employed in cosmetic formulations such as surface active agents, for example, nonionic or anionic surfactants, thickening agents and auxiliary solvents such as ethanol, glycol ethers and the like.

At the time of use, the anhydrous compositions of the present invention can be admixed with ammoniacal solutions which can optionally contain surface active agents, thickening agents, sequesterants and auxiliary solvents.

When the anhydrous hydrogen peroxide solutions of the present invention are used in bleaching and dyeing operations, the compositions containing them can be left in contact with the hair for a period of time ranging between 5 and 45 minutes.

When the anhydrous hydrogen peroxide solutions of the present invention are used in compositions for the second stage of a permanent wave operation or in the uncurling or straightening of the hair, the composition is left in contact with the hair for a period of time ranging from 5 to 20 minutes.

It has been observed that with the anhydrous compositions according to the present invention, there is obtained, in the case of bleaching the hair, a hair lightening which is stronger than when an aqueous solution of hydrogen peroxide in the same strength is employed.

The present invention also relates to an essentially anhydrous solution of hydrogen peroxide in at least one organic solvent, the said solvent comprising, essentially, a polyether oligomer of formula I and preferably the dimethyl ether of polytetrahydrofuran of formula II above, the said solution containing from 0.1 to 20% by weight of hydrogen peroxide and less than 1 percent by weight of water.

Preferably, the essentially anhydrous solution based on the polyether oligomer has a hydrogen peroxide content between 1 and 10 weight percent and a water content lower than 0.5 percent.

The following non-limiting examples illustrate the preparation of anhydrous solutions of hydrogen peroxide, as well as the use of these solutions in therapeutic and cosmetic formulations.

EXAMPLE 1

Solution of Hydrogen Peroxide in Dimethyl Ether of Polytetrahydrofuran

To a stirred solution of 500 ml of dimethyl ether of polytetrahydrofuran, having a viscosity of 22 centipoises at 25° C., there are slowly added, while cooling, 500 ml of a 60% solution of oxygenated water (200 volumes).

The heterogeneous mixture is maintained under good stirring for 3½ hours, at which point 50 g of sodium chloride are added and stirring is continued for ½ hour.

The organic phase is then decanted, dried on anhydrous sodium sulfate and then filtered.

The amount of hydrogen peroxide ($H_2O_2$) is determined by polarography: weight—15%.

A stability study over a 4 month period did not evidence any variation of the hydrogen peroxide content of the solution.

The dimethyl ether of tetrahydrofuran having a viscosity of 22 centipoises at 25° C. is obtained according to the following procedures:

In a 20 liter reactor fitted with a stirrer, a condenser, a thermometer and a nitrogen lead-in tube, there are introduced 5.32 kg of distilled tetrahydrofuran and 5.8 kg of methyl orthoformiate, also distilled.

The mixture is then stirred under a nitrogen atmosphere and cooled to 13° C.

120 ml of trifluoromethane sulfonic anhydride are then added to initiate polymerization. After 4 hours, at 18°–20° C., the catalyst is deactivated by 120 g of pure soda in solution in 600 ml of permutted water. The volatile products are then expelled under a vacuum at 80° C. After cooling, 6 liters of distilled cyclohexane and 120 g of powdered carbon black are introduced and the mixture is stirred for one hour. The mixture is then filtered by rinsing the precipitate with distilled cyclohexane.

The filtrate is then stirred under a vacuum initially at 50° C., then at 80° C. and finally at 100° C. to remove the solvent as well as fractions of volatile polyethers. 3.75 kg of an oily and colorless compound are recovered.

The oil obtained has a dynamic viscosity at 25° C. of 22 centipoises and solidifies at −1° C.

EXAMPLE 2

Solution of Hydrogen Peroxide in Amyl Alcohol

To a stirred solution of 500 ml of amyl alcohol, there are slowly added, while cooling, 500 ml of a 60% solution of oxygenated water (200 volumes).

The heterogeneous solution is maintained under good stirring for 4 hours at which point 50 g of sodium chloride are added and the stirring is continued for one hour.

The organic phase is then decanted, dried on sodium sulfate and filtered. The amount of hydrogen peroxide is determined by polarography. Amount—7.6%

EXAMPLE 3

Solution of Hydrogen Peroxide in Oleyl Alcohol

According to the same procedure as that described in Example 2, the extraction by oleyl alcohol provides an anhydrous solution of hydrogen peroxide having a content of 4.5%.

EXAMPLE 4

Solution of Hydrogen Peroxide in Polyethylene Glycol (PEG 200)

To 400 ml of ethyl ether there are added, with stirring, at 20° C., 400 ml of 60% oxygenated water (200 volumes).

After stirring the mixture for about 1 hour, sodium chloride is added up to saturation. The ether phase is then decanted and dried on anhydrous sodium sulfate.

After filtration, there are added to the solution of hydrogen peroxide in ether, 100 ml of polyethylene glycol (PEG 200) at a temperature of 20° C. After stirring, the ether is evaporated and there is obtained a clear, anhydrous solution of hydrogen peroxide in polyethylene glycol having a $H_2O_2$ content of 12.5%.

EXAMPLE 5

Solution of Hydrogen Peroxide in Methoxy Propanol

As described above in Example 4, a solution of hydrogen peroxides in ethyl ether is prepared starting with 200 ml of ether and 200 ml of 60% oxygenated water.

To this solution there are added at 20° C. with stirring 100 ml of methoxypropanol ("DOWANOL PM", sold by Dow Chemical).

After evaporating the ether, an anhydrous solution of hydrogen peroxide in methoxy propanol having an $H_2O_2$ content of 4.9% is obtained.

ANTI-ACNE COMPOSITIONS

Example A

| | |
|---|---|
| 15% anhydrous solution of hydrogen peroxide in dimethyl ether of polytetrahydrofuran of Example 1 | 20 g |
| diemthylether of polytetrahydrofuran-viscosity of 22 centipoises at 25° C. | 80 g |

The resulting solution has a content of 3% of hydrogen peroxide and possesses comedolytic properties equivalent to those of a 6% solution of benzoyl peroxide.

Example B

| | |
|---|---|
| 15% anhydrous solution of hydrogen peroxide in dimethylether of polytetrahydrofuran of Example 1 | 25 g |
| monoethyl ether of diethylene glycol | 75 g |

The resulting anhydrous solution has a hydrogen peroxide content of 3.75%.

Example C

| | |
|---|---|
| 15% anhydrous solution of hydrogen | 25 g |

-continued

| | |
|---|---|
| peroxide in dimethylether of polytetrahydrofuran of Example 1 | |
| n-propyl alcohol | 36 g |
| isopropyl alcohol | 36 g |
| hydroxypropyl cellulose | 3 g |

This anhydrous gel exhibit good comedolytic activity which has been confirmed by the rhino mouse test.

Example D

| | |
|---|---|
| 15% anhydrous solution of hydrogen peroxide in dimethylether of polytetrahydrofuran of Example 1 | 40 g |
| n-propyl alcohol | 40 g |
| propylene glycol | 18 g |
| hydroxypropyl cellulose | 2 g |

Examples E to K

| Example | E | F | G | H | I | J | K |
|---|---|---|---|---|---|---|---|
| 12.9% soln of $H_2O_2$ in dimethyl ether of polytetrahydrofuran | 24 | — | 24 | — | — | 24 | 24 |
| 12.5% soln of $H_2O_2$ in polyethylene glycol | — | 24 | — | 24 | — | — | — |
| 4.9% soln of $H_2O_2$ in methoxypropanol | — | — | — | — | 63 | — | — |
| o-oxyquinolein sulfate | 0.02 | 0.02 | 0.02 | 0.02 | 0.02 | 0.02 | 0.02 |
| Phenacetin | 0.05 | 0.05 | 0.05 | 0.05 | 0.05 | 0.05 | 0.05 |
| Citric acid | 0.2 | 0.2 | 0.2 | 0.2 | 0.2 | 0.2 | 0.2 |
| Salicylic acid | 0.2 | 0.2 | 0.2 | 0.2 | 0.2 | 0.2 | 0.2 |

| Example | E | F | G | H | I | J | K |
|---|---|---|---|---|---|---|---|
| Absolute ethyl alcohol | 60.4 | — | — | — | — | 60.4 | — |
| Isopropanol | — | 60.4 | 60.4 | 60.4 | — | — | 37.7 |
| Methoxy propanol | — | — | — | — | 21.43 | — | — |
| Polyethylenated oleic glycerides ("LABRAFILM 1944CS") | — | 15.13 | — | — | 15.1 | 15.13 | — |
| Polyethylenated $C_8$-$C_{10}$ glycerides ("LABRASOL") | — | — | 15.13 | — | — | — | — |
| Triglycerides of fatty acids ("Miglyol 812") | 15.13 | — | — | 15.13 | — | — | — |
| Volatile silicone | — | — | — | — | — | — | 37.83 |

Example L

Hair Bleaching Composition

| | |
|---|---|
| Composition 1 | |
| 8.8% anhydrous solution of hydrogen peroxide in dimethylether of poly tetrahydrofuran | 68 g |
| Nonyl phenol oxyethylenated with 9 moles of ethylene oxide | 27 g |
| ethyl alcohol | 5 g |
| | 100 g |
| Composition 2 | |
| Ammonia, 22° Be | 100 g |

At the time of use, 90 g of Composition 1 are mixed with 10 g of Composition 2.

The resulting liquid and homogeneous mixture is left in contact with chestnut colored hair for 20 minutes.

After rinsing and drying, a strong discoloration or bleaching of the hair is achieved.

Example M

Hair Bleaching Composition

| | |
|---|---|
| Composition 1 | |
| 9.8% anhydrous solution of hydrogen peroxide in dimethylether of poly-tetrahydrofuran | 61 g |
| Texapon WW 99 (lauryl sulfate of monoisopropanolamine), sold by Henkel | 10 g |
| ethyl alcohol | 29 g |
| | 100 g |
| Composition 2 | |
| Oleyl alcohol glycerolated with 2 moles of glycerol | 5 g |
| Oleyl alcohol glycerolated with 4 moles of glycerol | 5 g |
| Oleic acid | 5 g |
| Oleic diethanolamine | 5 g |
| Oleic diethanolamide | 12 g |
| Ethyl alcohol | 10 g |
| Ethyl glycol | 12 g |
| EDTA | 0.2 g |
| Ammonia, 22° Be | 11 g |
| Water, sufficient amount for | 100 g |

At the time of use, 2 parts of Composition 1 are mixed with 1 part of Composition 2.

The resulting homogeneous mixture is left in contact with chestnut colored hair for 30 minutes.

After rinsing and drying, a medium lightening of the hair is achieved.

Example 2

Hair Dyeing Composition

| | |
|---|---|
| Composition 1 | |
| paraphenylene diamine | 0.185 g |
| paraaminophenyl | 0.555 g |
| 1-methyl-2-hydroxy-4-hydroxy ethylamine benzene | 0.308 g |
| 2,4 diaminophenoxy ethanol dihydrochloride | 0.123 g |
| ethanol | 20.4 g |
| ammonium thiolactate (at 50% in equivalent of thiolactic acid) | 17.9 g |
| ammonia, 20% of NHs | 6.16 g |
| demineralized water, sufficient amount for | 100 g |
| Composition 2 | |
| 15.8% anhydrous solution of hydrogen peroxide in dimethylether of poly-tetrahydrofuran | 100 g |

At the moment of use, 81 g of Composition 1 are mixed with 19 g of Composition 2.

The resulting mixture is then applied to natural hair having 90% white hair. After 30 minutes of contact the hair is rinsed, shampooed and dried.

The color of the thus treated hair is light chestnut bordering on mahogany.

Example O

Permanent wave composition

| The following reducing composition is applied to the hair: | |
|---|---|
| thioglycolic acid | 6 g |
| Ammonia, sufficient amount for pH = 9.5 | |
| sequestering agent | 0.2 g |
| fatty alcohol polyoxyethylenated with 20 moles of ethylene oxide | 1 g |
| perfume | 0.5 g |
| water, sufficient amount for | 100 g |

The hair is impregnated once with the above composition and is then rolled up on hair rollers. The composition is left in contact with the hair for 10 to 15 minutes.

After rinsing, the following oxidizing solution is applied to the hair:

| | |
|---|---|
| 9.8% anhydrous solution of hydrogen peroxide in dimethylether of polytetrahydrofuran | 61 g |
| Texapon WW 99 (lauryl sulfate of monoisopropanolamine, sold by Henkel) | 10 g |
| ethyl alcohol | 29 g |

This composition is left in contact with the hair for 5 minutes at which point the hair is rinsed and the rollers are removed.

An excellent permanent is achieved and the hair is soft to the touch and lively.

What is claimed is:

1. An essentially anhydrous solution of hydrogen peroxide in an organic solvent comprising a polyether oligomer, said polyether oligomer being the dimethylether of polytetrahydrofuran having the formula

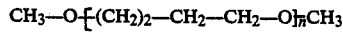

n has a mean value ranging from 4 to 10, and the said solution contains from 1 to 10 weight percent of hydrogen peroxide and less than 0.5 weight percent of water.

2. A process for the treatment of acne comprising applying to the skin an effective amount to treat acne of an essentially anhydrous solution of hydrogen peroxide in a polyether oligomer selected from the group consisting of (i) a polyether oligomer of ethylene oxide, (ii) a polyether oligomer of propylene oxide, (iii) the ether of (i), (iv) the ether of (ii) and (v) a polyether oligomer having the formula

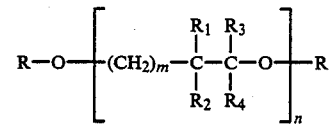

wherein
R represent linear or branched alkyl having 1-12 carbon atoms,
$R_1$, $R_2$, $R_3$ and $R_4$ each independently represent hydrogen or alkyl having 1-6 carbon atoms, with at least two of $R_1$, $R_2$, $R_3$ and $R_4$ being hydrogen,
m is 1-4,
n has a mean value greater than or equal to 2, and the number of carbon atoms in each repeating unit, independently, being at least equal to 4,
said solution containing from 0.1 to 20 percent by weight of hydrogen peroxide and less than 1 weight percent of water.

3. The process of claim 2 wherein n is between 4 and 50.

4. The process of claim 2 wherein said polyether oligomer is the dimethylether of polytetrahydrofuran having the formula

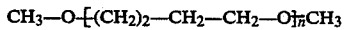

wherein n has a mean value between 4 and 10.

5. A process for the treatment of acne comprising applying to the skin an effective amount to treat acne of an essentially anhydrous solution of hydrogen peroxide in an organic solvent selected from the group consisting of an alcohol having 2-20 carbon atoms, a polyol, an ether oxide, an acid ester having the formula R'COOR" wherein R' is a hydrocarbon radical having 1-21 carbon atoms and R" is a hydrocarbon radical having 1-22 carbon atoms, a triglyceride of fatty acids having 6-22 carbon atoms and an N-alkyl lactam, said solution containing from 0.1 to 20 weight percent of hydrogen peroxide and less than 1 weight percent of water.

6. The process of claim 5 wherein said hydrogen peroxide is present in an amount ranging from 1 to 10 weight percent and water is present in an amount lower than 0.5 weight percent.

7. The process of claim 5 wherein said alcohol is selected from the group consisting of ethanol, n-propanol, amyl alcohol, isopropanol, oleyl alcohol, cyclohexanol and benzyl alcohol.

8. The process of claim 5 wherein said polyol is selected from the group consisting of ethylene glycol, propylene glycol, diethylene glycol, glycerol and ethers thereof.

9. The process of claim 5 wherein said ether oxide is selected from the group consisting of ethyl ether, isopropyl ether and dioxane.

10. The process of claim 5 wherein said acid ester is selected from the group consisting of ethyl acetate, butyl acetate, isopropyl myristate, isopropyl palmitate, isopropyl linoleate, arachidonyl propionate and jojoba oil.

11. The process of claim 5 wherein said N-alkyl lactam is N-methyl pyrrolidone.

* * * * *